(12) United States Patent
Swenson et al.

(10) Patent No.: US 11,583,681 B2
(45) Date of Patent: Feb. 21, 2023

(54) LEADLESS PACEMAKER AND METHOD FOR STORING EVENT DATA IN A LEADLESS PACEMAKER

(71) Applicant: BIOTRONIK SE & Co. KG, Berlin (DE)

(72) Inventors: Kurt Swenson, Dayton, OR (US);
Brian M. Taff, Portland, OR (US);
Brad McMillan, Lake Oswego, OR (US); Karl-Heinz Freiberg, Woodburn, OR (US); David Miller, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 176 days.

(21) Appl. No.: 17/083,965

(22) Filed: Oct. 29, 2020

(65) Prior Publication Data
US 2021/0170181 A1 Jun. 10, 2021

Related U.S. Application Data

(60) Provisional application No. 62/943,282, filed on Dec. 4, 2019.

(51) Int. Cl.
*A61N 1/37* (2006.01)
*A61N 1/372* (2006.01)
(Continued)

(52) U.S. Cl.
CPC ......... *A61N 1/3704* (2013.01); *A61N 1/3706* (2013.01); *A61N 1/3756* (2013.01);
(Continued)

(58) Field of Classification Search
CPC ...... A61N 1/057; A61N 1/362; A61N 1/3704; A61N 1/3706; A61N 1/372;
(Continued)

(56) References Cited

U.S. PATENT DOCUMENTS 5,709,712 A 1/1998 Paul et al.
2001/0041918 A1 11/2001 Baker et al.
(Continued)

FOREIGN PATENT DOCUMENTS

WO WO 82/02836 * 9/1982 ............... A61N 1/36

OTHER PUBLICATIONS

European Search Report and Annex to the European Search Report on European Patent Application No. EP 20153193.6, dated Jul. 10, 2020 (8 pages).

*Primary Examiner* — Brian T Gedeon
(74) *Attorney, Agent, or Firm* — Buchanan Ingersoll & Rooney PC

(57) ABSTRACT

A leadless pacemaker, and method for storing event data therein, comprising a central processing unit, a first logic circuit configured to generate event data based on a first event occurring during operation of the leadless pacemaker, a first hardware event counter configured to be incremented if specific event data are generated by said first logic circuit, a first memory unit comprising a first bit configured to be set if said first hardware event counter is incremented to a first maximum number of counts, a second memory unit communicating with said first memory unit, wherein said central processing unit is configured to transfer said first bit to said second memory unit, a first RAM event counter in a random access memory of said leadless pacemaker, wherein said central processing unit is configured to increment said first RAM event counter if said first bit is transferred to the second memory unit.

15 Claims, 2 Drawing Sheets

(51) Int. Cl.
*A61N 1/375* (2006.01)
*G16H 40/60* (2018.01)
(52) U.S. Cl.
CPC ..... *A61N 1/37252* (2013.01); *A61N 1/37512* (2017.08); *G16H 40/60* (2018.01)
(58) Field of Classification Search
CPC ............ A61N 1/37252; A61N 1/37512; A61N 1/3756; A61N 1/39622; G16H 20/40; G06F 11/1047; G06F 11/3024; G06F 9/3012
See application file for complete search history.

(56) References Cited

U.S. PATENT DOCUMENTS

2008/0046700 A1* 2/2008 Gara ..................... G06F 11/348
712/227
2017/0281033 A1* 10/2017 Higgins ............... A61N 1/3987

* cited by examiner

LEADLESS PACEMAKER AND METHOD FOR STORING EVENT DATA IN A LEADLESS PACEMAKER

CROSS-REFERENCE TO RELATED APPLICATIONS

This patent application claims the benefit of and priority to U.S. Provisional Patent Application No. 62/943,282, filed on Dec. 4, 2019, which is hereby incorporated by reference in its entirety.

TECHNICAL FIELD

The present invention relates to a leadless cardiac pacemaker and a method for storing event data in a leadless cardiac pacemaker.

BACKGROUND

Pacemakers are implantable devices which deliver electrical pulses to the heart to stimulate the heart and maintain cardiac rhythm in patients with heart disease.

In contrast to traditional pacemakers which are implanted in a subcutaneous location, leadless pacemakers are small enough to be directly implanted into the heart, and therefore lack electrical leads guided from the pacemaker to the heart.

To monitor and optimize performance and monitor patient health, some pacemakers are capable of detecting, counting and storing events occurring during operation of the pacemaker. From the stored event data, pacemaker statistics, such as event counters, histograms (consisting of a series of categorized counters) and trends can be derived.

The typical means of collecting and storing data in a pacemaker according to the prior art is to use an event-driven central processing unit (CPU) to process events and to analyze and categorize them into counts, trends and histograms (so-called CPU-centric approach). Therein, the CPU typically stores the resulting data in random access memory (RAM) which can be interrogated by a clinical programmer and processed for display to the user.

Pacemaker events occur every cardiac cycle. Waking the CPU to handle each event requires a significant overhead to manage context switching. Making timing measurements related to the events can require CPU performance levels that can make the energy expenditures for the CPU higher than desired, such as needing to support higher clock rates and to include extra timing peripheral components and to handle complicated software algorithms that keep the CPU active for longer time periods.

The CPU-centric approach has a high impact on service time of pacemakers. Moreover, an alternative approach using dedicated logic to do the collection and storage of the data would increase the size of the integrated circuit, potentially impacting the volume of the pacemaker.

The present invention is directed toward overcoming one or more of the above-mentioned problems, though not necessarily limited to embodiments that do.

SUMMARY

Therefore, an objective of the present invention is to provide a leadless pacemaker and a method for storing event data in a leadless pacemaker which are improved in view of the described drawbacks of the prior art, in particular pacemakers which are able to store short term statistical data without needing to invoke CPU operations, and without putting tight tolerances on the timing abilities of the CPU.

At least this objective is obtained by the subject matter of the independent claims 1 (leadless pacemaker) and 11 (method). Advantageous embodiments of the present invention are claimed as dependent claims 2 to 10 and 12 to 15 and are described hereafter.

A first aspect of the present invention relates to a leadless pacemaker comprising at least the following components:
- a central processing unit configured to control an operation of the leadless pacemaker,
- a first logic circuit configured to generate event data based on a first event occurring during operation of the leadless pacemaker,
- a first hardware event counter configured to be incremented if specific event data are generated by the first logic circuit,
- a first memory unit comprising a first bit configured to be set, particularly from 0 to 1, if the first hardware event counter is incremented to a first maximum number of counts,
- a second memory unit communicating with the first memory unit, wherein the central processing unit is configured to transfer the first bit from the first memory unit to the second memory unit, and
- a first RAM event counter in a random access memory of the leadless pacemaker, wherein the central processing unit is configured to increment the first RAM event counter if the first bit is transferred to the second memory unit.

Within the context of the present specification, the term "leadless pacemaker" designates an artificial cardiac pacemaker implantable directly into the heart.

A "CPU", or "central processing unit" as used herein is a microprocessor configured to control the operation of the leadless pacemaker, which may include controlling the generation of a voltage at a pacing electrode of the leadless pacemaker, and controlling the sensing of electrical signals of the heart as well as general control and organization of data processing.

The term "logic circuit" in the context of the present specification means a hardware component executing a processing function in an embedded system of the leadless pacemaker according to the present invention. In particular, the logic circuit may incorporate selector logics configured to process two binary inputs into one binary output. Since they are hardware components, the logic circuits described herein function independently of the CPU and without triggering a CPU task. The logic circuits may receive input data related to the events occurring during operation of the leadless pacemaker, particularly from sensors or from other components of the embedded system of the leadless pacemaker. These input data are processed by the respective logic circuit, thereby generating event data as described below.

As used herein, the term "event data" describes any data associated with and representing events occurring during operation of the leadless pacemaker.

In the context of the present specification, the term "hardware event counter" designates a hardware component comprising a memory configured to count the number of inputs to the hardware event counter. For instance, in case of simple event data, the hardware event counter may receive an input signal, each time a pace is delivered by the pacing electrode of the leadless pacemaker. Each time an input signal occurs, bits in the memory of the hardware event counter are set, particularly from 0 to 1, in a manner that the number of received input signals is counted, in other words, the hardware event counter is incremented. The hardware event counter has a limited bit size or storage space, resulting in a maximum number of counts that can be counted by the hardware event counter. Therein, in particular, the size of the hardware event counter is determined to be sufficient to cover the number of expected events in a particular time period, wherein this time period is optimized to contribute towards the minimum volume of the leadless pacemaker with the maximum service time. Importantly, the hardware event counters are hardware components which are able to operate independently of the CPU and without triggering a CPU task.

The term "memory unit" (such as, e.g., the first and the second memory unit) in the context of the present specification means a unit for storing information in a computer system. For instance, a memory unit as used herein, may be a register or latch. A "register" or "processor register" is a quickly accessible location in storage available to the CPU of the leadless pacemaker. The term "latch" describes an electronic circuit that has two stable states and can be used to store information.

The corresponding bit, for example, the first bit mentioned above, is transferred from the first memory unit to the second memory unit by means of the CPU. In other words, a bit in the second memory unit is set, particularly from 0 to 1, and the bit in the first memory unit set upon overflow of the respective hardware event counter is cleared, particularly set from 1 to 0.

As used herein, the term "RAM event counter" describes a dedicated area in the system's random access memory defined by the CPU configured to count specific inputs. The CPU generates these inputs into the respective RAM event counter based on bits set in the second memory unit. According to the present invention, this procedure is used to count and store in the RAM event counter the number of times a specific hardware event counter has overflowed. If the maximum number of counts of the respective hardware event counter is known, the total number of events equals the product of the total number of counts of the respective RAM event counter times the maximum number of counts of the respective RAM event counter plus the counts of the respective hardware event counter.

When the maximum number of counts of the respective hardware event counter is reached, in other words, when the memory of the hardware event counter overflows, a corresponding first bit is set, particularly from 0 to 1, in the first memory unit, particularly in the register or latch, wherein particularly the hardware event counter wraps around to zero, in other words resets, at the same time or shortly after, wherein the counts stored in the hardware event counter are cleared.

Storing the statistical data of the leadless pacemaker in RAM cells takes up much less silicon area in an integrated circuit than the equivalent registers, such that a large amount of data can be stored in a small size pacemaker. In addition, the described architecture of the embedded system allows storage of the statistical data using less CPU tasks than required in leadless pacemakers of the prior art. This is achieved by using hardware elements (hardware event counters) for actual event counting, whereas a CPU task is only required to transfer the corresponding bits representing overflow events of the hardware event counters to random access memory.

In certain embodiments, the leadless pacemaker further comprises a second logic circuit configured to generate event data based on a second event occurring during operation of the leadless pacemaker, and the leadless pacemaker comprises a second hardware event counter configured to be incremented if specific event data are generated by the second logic circuit, wherein the first memory unit comprises a second bit configured to be set if the second hardware event counter is incremented to a second maximum number of counts, and wherein the central processing unit is configured to transfer the second bit from the first memory unit to the second memory unit, and wherein the leadless pacemaker comprises a second RAM event counter in the random access memory of the leadless pacemaker, wherein the central processing unit is configured to increment the second RAM event counter if the second bit is transferred from the first memory unit to the second memory unit.

In certain embodiments, the leadless pacemaker comprises at least one further logic circuit configured to generate event data based on a further event occurring during operation of the leadless pacemaker, and the leadless pacemaker comprises at least one further hardware event counter configured to be incremented if specific event data are generated by the further logic circuit, wherein the first memory unit comprises a further bit configured to be set if the further hardware event counter is incremented to a further maximum number of counts, and wherein the central processing unit is configured to transfer the further bit from the first memory unit to the second memory unit, and wherein the leadless pacemaker comprises at least one further RAM event counter in the random access memory of the leadless pacemaker, wherein the central processing unit is configured to increment the further RAM event counter if the further bit is transferred from the first memory unit to the second memory unit.

In other words, the leadless pacemaker may also comprise any number of further logic circuits and further associated hardware event counters having the properties of the above described first and second logic circuits and hardware event counters.

By utilizing more than one logic circuit and hardware event counter, different events occurring during the operation of the leadless pacemaker may be detected, counted and stored.

In certain embodiments, the first event is describable by a binary variable, wherein the event data generated from the first event are values or characteristics of the binary variable.

In certain embodiments, the second event or the further event is describable by a binary variable, wherein the event data generated from the second event or the further event are values or characteristics of the binary variable.

A binary variable in the context of the present specification is a variable having two possible values, such as 0 and 1. Such a variable is commonly represented by a bit. In particular, the value of the binary variable represents whether a certain event has occurred or not. For instance, a value of 1 of a certain binary variable may represent the fact that a pace has been delivered by the pacing electrode of the leadless pacemaker.

In certain embodiments, the first event is describable by a first binary variable and a second binary variable, wherein the event data generated from the first event is a third binary variable representing a specific combination of the values of the first binary variable and the second binary variable.

In certain embodiments, the second event or the further event is describable by a first binary variable and a second binary variable, wherein the event data generated from the first event is a third binary variable representing a specific combination of the values of the first binary variable and the second binary variable.

For example, it is possible to implement a logic gate, such as an OR-gate or an AND-gate using this embodiment. In this case, the value of the third binary variable may be set to 1 if either the value of the first binary variable or the value of the second binary variable is 1 (OR-gate) or the value of the third binary variable may be set to 1 if both the value of the first binary variable and the value of the second binary variable is 1 (AND-gate).

In this manner, combinations of events occurring during operation of the leadless pacemaker can be tracked in the form of event data. For example, the number of cardiac cycles with an atrial sense and a ventricular pace may be counted (implementing the AND-gate).

In certain embodiments, the first event is describable by a binary variable and a metric variable, wherein the event data generated from the first event represents a combination of a value of the binary variable and a range of the metric variable.

In certain embodiments, the second event or the further event is describable by a binary variable and a metric variable, wherein the event data generated from the second event or the further event represents a combination of a value of the binary variable and a range of the metric variable.

Values of the metric variable may be, e.g., integers or floats. In particular, the metric variable represents measured parameters, such as a voltage detected by a sensor or a time period measured using a clock of the embedded system.

In particular, the events represented by the binary variable and the range of the metric variable may be events belonging a certain category of a histogram, such as atrial senses with an interval between 900 ms and 1000 ms, or atrial senses with an interval between 1000 ms and 1100 ms. From such event data, histograms can be generated by detecting and counting events in different categories.

In certain embodiments, leadless pacemaker comprises a clock configured to generate clock data.

Advantageously, a system clock allows to optimize the timing of steps during detecting events and counting and storing event data in the pacemaker to contribute towards a small volume of the leadless pacemaker with a maximum service life. The optimal timing for setting the RAM event counters can be determined using the system clock.

In certain embodiments, the first memory unit is double buffered, such that its contents are transferrable to the second memory unit while clearing the first memory unit in a single operation, wherein the operation is clocked based on the clock data.

This further reduces necessary CPU tasks and contributes to a small size and long service life of the leadless pacemaker.

In certain embodiments, the central processing unit is configured to periodically transfer the first bit and/or the second bit to the second memory unit.

This process can also be timed optimally to contribute towards the minimum volume and maximum service life of the pacemaker.

In certain embodiments, the first hardware event counter and/or the second hardware event counter is memory mapped or I/O-mapped.

Therein, the term "memory mapped" means that the content of the first hardware event counter and/or the second hardware event counter (representing the counts of the first and/or second hardware event counter) are mapped to the random access memory of the leadless pacemaker.

The term "I/O-mapped" means that the content of the first hardware event counter and/or the second hardware event counter (representing the counts of the first and/or second hardware event counter) are assigned to an I/O port address, such that the content of the first hardware event counter and/or the second hardware event counter may be mapped onto an external device connected to the respective I/O port of the leadless pacemaker.

By means of memory mapping or I/O mapping, an external clinical programmer can easily read out the contents of the pacemaker's hardware event counters. Together with the readout of the RAM blocks representing the RAM event counters, the total number of events can be accurately determined at any time by calculating the product of the maximum number of counts of the respective hardware counter and the overflow events stored in the respective RAM event counter, and adding any remaining counts in the respective hardware event counter.

In certain embodiments, the first memory unit and/or the second memory unit is a register or a latch, wherein particularly the second memory unit is a tristate latch. Therein, the term "tristate latch" describes a latch which is able to assume three states (0, 1, and high impedance).

A second aspect of the present invention relates to a method for storing event data in a leadless pacemaker, particularly a leadless pacemaker according to the first aspect of the invention, wherein event data are generated based on a first event occurring during operation of the leadless pacemaker, and wherein a first hardware counter is incremented if specific event data are generated based on the first event, and wherein a first bit in a first memory unit is set if the first hardware event counter is incremented to a first maximum number of counts, an wherein the first bit is transferred from the first memory unit to a second memory unit, and wherein a first RAM event counter in a random access memory of the leadless pacemaker is incremented if the first bit is transferred from the first memory unit to the second memory unit.

In certain embodiments of the method, further event data are generated based on a second event occurring during operation of the leadless pacemaker, wherein a second hardware counter is incremented if specific event data are generated based on the second event, and wherein a second bit in the first memory unit is set if the second hardware event counter is incremented to a second maximum number of counts, and wherein the second bit is transferred from the first memory unit to a second memory unit, and wherein a second RAM event counter in the random access memory of the leadless pacemaker is incremented if the second bit is transferred from the first memory unit to the second memory unit.

In certain embodiments of the method, further event data are generated based on at least one further event occurring during operation of the leadless pacemaker, wherein a further hardware counter is incremented if specific event data are generated based on the further event, and wherein a further bit in the first memory unit is set if the further hardware event counter is incremented to a further maximum number of counts, and wherein the further bit is transferred from the first memory unit to a second memory unit, and wherein a further RAM event counter in the random access memory of the leadless pacemaker is incremented if the further bit is transferred from the first memory unit to the second memory unit.

In certain embodiments of the method, the first event is describable by a binary variable, wherein the event data generated from the first event are values or characteristics of the binary variable, wherein particularly the first event is a pace delivered by the leadless pacemaker or a ventricular sense detected by the leadless pacemaker.

In certain embodiments, the first event is describable by a first binary variable and a second binary variable, wherein the event data generated from the first event is a third binary variable representing a specific combination of the values of the first binary variable and the second binary variable, particularly wherein the first event is a cardiac cycle with an atrial sense and a ventricular pace.

In certain embodiments, the second event or the further event is describable by a first binary variable and a second binary variable, wherein the event data generated from the second event or the further event is a third binary variable representing a specific combination of the values of the first binary variable and the second binary variable, particularly wherein the second event or the further event is a cardiac cycle with an atrial sense and a ventricular pace.

In certain embodiments, the first event is describable by a binary variable and a metric variable, wherein the event data generated from the first event represents a combination of a value of the binary variable and a range of the metric variable, particularly wherein the first event is a cardiac cycle with an atrial sense and a time interval between atrial senses within a specific range.

In certain embodiments, the second event or the further event is describable by a binary variable and a metric variable, wherein the event data generated from the second event or the further event represents a combination of a value of the binary variable and a range of the metric variable, particularly wherein the second event or the further event is a cardiac cycle with an atrial sense and a time interval between atrial senses within a specific range.

Wherever alternatives for single separable features are laid out herein as "embodiments", it is to be understood that such alternatives may be combined freely to form discrete embodiments of the present invention disclosed herein.

Additional features, aspects, objects, advantages, and possible applications of the present invention will become apparent from a study of the exemplary embodiments and examples described below, in combination with the Figures and the appended claims.

BRIEF DESCRIPTION OF THE DRAWINGS

The present invention is further illustrated by the following examples and figures, from which further embodiments and advantages can be drawn. These examples are meant to illustrate the invention but not to limit its scope.

DETAILED DESCRIPTION

Figure 1:
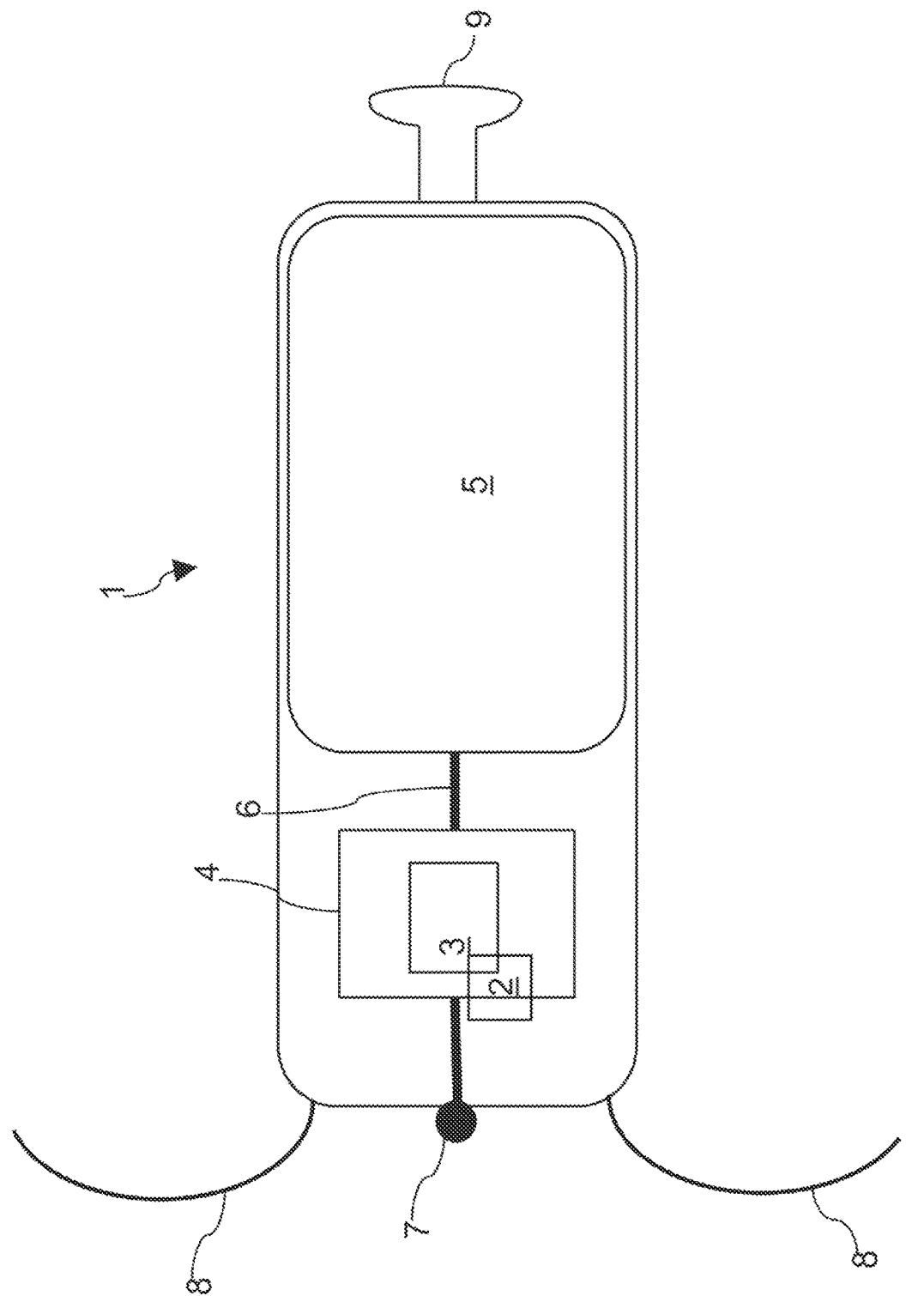
FIG. 1 shows a schematic sectional view of an example of a leadless pacemaker according to the present invention.

FIG. 1 shows in a sectional view a leadless pacemaker comprising an electronic module 4, an energy storage 5 and an electrical connection 6 connecting the energy storage 5 to the electronic module 4 to supply energy to the electronic module 4. The leadless pacemaker 1 further comprises an electrode 7 configured to be brought into contact with cardiac tissue when the leadless pacemaker 1 is implanted into a heart, wherein the electrode 7 is configured to generate an electric pulse and stimulate the heart. In addition, the pacemaker 1 comprises fixation elements 8 (here displayed as hooks) for fixing the leadless pacemaker 1 in the cardiac tissue. An implant/explant port 9 of the leadless pacemaker 1 is also displayed in FIG. 1.

Figure 2:
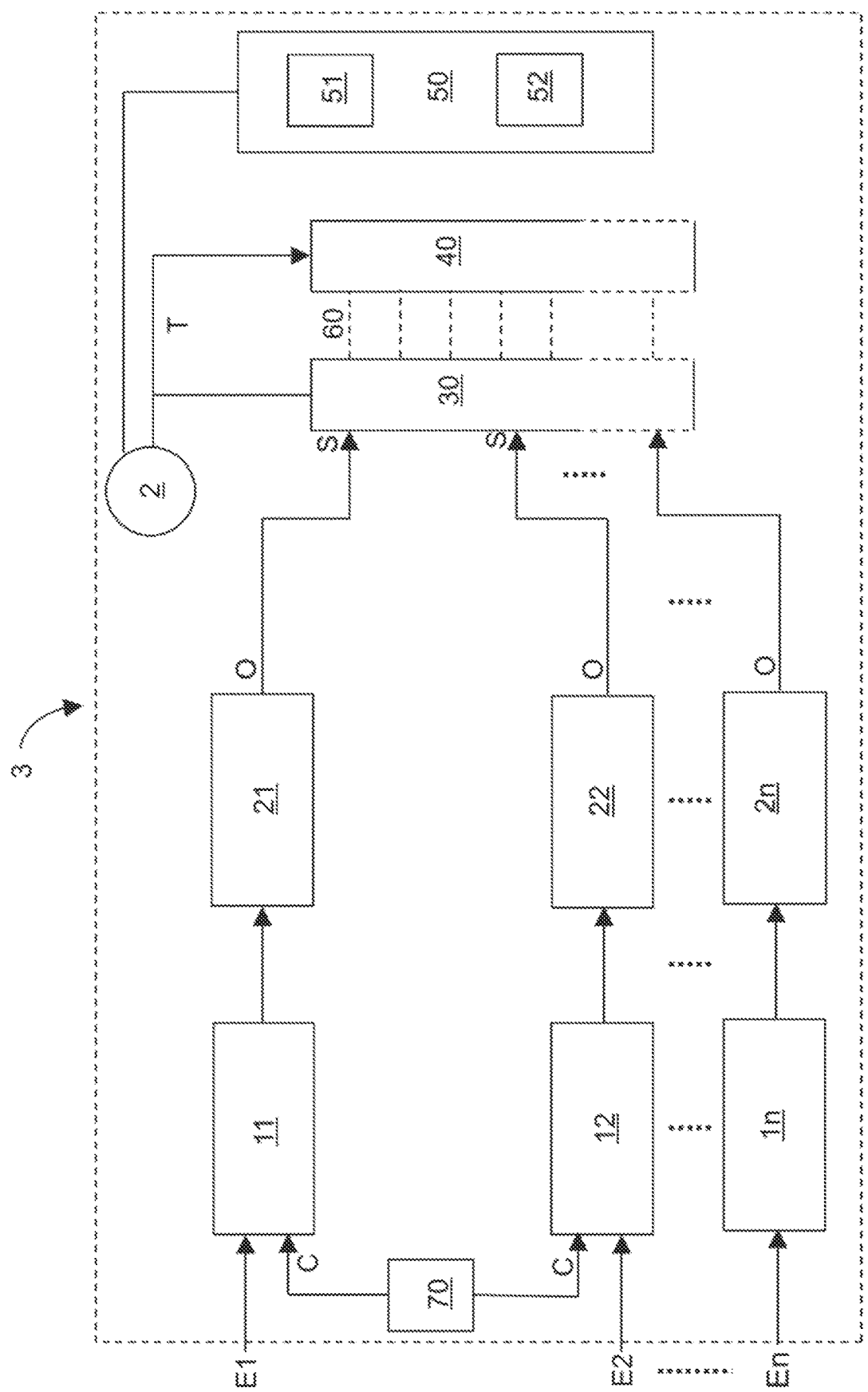
FIG. 2 shows a schematic diagram of an embedded system comprised in the leadless pacemaker according to the present invention.

The electronic module 4 of the leadless pacemaker 1 comprises an embedded system 3 comprising a central processing unit (CPU) 2, the embedded system 3 being depicted in detail in FIG. 2.

The embedded system 3 comprises a first logic circuit 11 which receives an input signal based on a first event E1 occurring during the operation of the leadless pacemaker 1, and a second logic circuit 12 receiving an input signal based on a second event E2 occurring during the operation of the leadless pacemaker 1. For instance, the input signals may be generated by sensors of the leadless pacemaker 1. Alternatively, the CPU 2 may provide input signals, e.g. each time the CPU 2 sends a control signal to the electrode 7 of the leadless pacemaker 1 to initiate pulse generation. Of course, the first logic circuit 11 and the second logic circuit 12 may each receive more than one signal in case of complex events E1, E2. The first logic circuit 11 and the second logic circuit 12 also receive clock data C from a clock 70 of the embedded system 3, such that the input signals based on the events E1, E2 can be timed.

The first logic circuit 11 and the second logic circuit 12 are configured to process the input signal or input signals and generate event data representing the events E1, E2 based on the input signals. For example, the first logic circuit 11 may be configured to generate event data representing a pace each time a pace has been generated by the electrode 7 of the leadless pacemaker. An output signal is then sent from the first logic circuit 11 to a first hardware event counter 21 if the event data indicate that a pace has been generated, thereby incrementing the first hardware event counter 21.

Likewise, the second logic circuit 12 may be adapted to generate event data representing whether a cardiac cycle with an atrial sense and a ventricular pace has occurred, and to send a respective output signal to a second hardware event counter 22, which is incremented accordingly.

Importantly, the first logic circuit 11, the second logic circuit 12, the first hardware event counter 21 and the second hardware event counter 22 are hardware components working independently of the CPU 2, which reduces the necessary CPU tasks. The first and second logic circuits 11, 12 are used to identify the event conditions that represent the statistics being collected. This may include logic that times the interval between events. In the case of histogram data, the logic, including for example the measured intervals, may be used to select which hardware event counter 21, 22 will be incremented using selector logic.

For simplicity, two logic circuits 11, 12 and two hardware event counters 21, 22 are depicted in FIG. 2. Of course, the embedded system 3 may contain more than two logic circuits configured to generate event data and more than two hardware event counters to count the events to detect and process further events.

The first hardware event counter 21 and the second hardware event counter 22 can each count to a respective maximum number of counts based on their allocated memory size. If this maximum number of counts is reached, overflow O of the first hardware event counter 21 or the second hardware event counter 22 occurs. During overflow O of a hardware event counter, an output signal is sent to a first memory unit 30, which may be an active register or a latch. Based on which hardware event counter 21, 22 generated the output signal, a corresponding bit in the first memory unit 30 is set from 0 to 1 (set operation S) and the respective hardware event counter 21, 22 is cleared, and may begin to count again.

The first memory unit 30 is double buffered. Periodically, at an optimized time period to contribute towards minimum volume and maximum service life of the leadless pacemaker 1, a CPU task is triggered which transfers the overflow bits in the first memory unit 30 to a second memory unit 40, which may be a working register or a tri-state latch (transfer operation T).

The overflow bits associated to the first hardware event counter 21 and the second hardware event 22 counter are transferred to the second memory unit 40 in a single clocked operation, which further reduces CPU tasks.

In particular, the first memory unit 30 and the second memory unit 40 are connected by a data bus 60 to transfer the corresponding bits.

For each of the hardware event counters 21, 22 in the embedded system 3, the CPU task defines storage space in the random access memory (RAM) 50 for counting how many overflows O have occurred for the respective hardware event counter 21, 22. In other words, a first RAM event counter SI counting the overflows O of the first hardware event counter 21 and a second RAM event counter 52 counting the overflows O of the second hardware event counter 22 are defined in the RAM 50. A CPU task sequentially finds which bits have been set in the second memory unit 40 and accordingly increments the associated first or second RAM event counter 51, 52. The allocated space in RAM 50 for each RAM event counter 51, 52 is sized to be able to count up to the maximum number of overflows O expected, either in the lifetime of the leadless pacemaker 1 or between follow-up inspections when the event count to yield statistics could be restarted.

In particular, the hardware event counters 21, 22 are cleared only at power up and when a command is received from an external programmer to restart the statistics. This command will particularly also cause the associated RAM event counters 51, 52 to be cleared.

The hardware event counters 21, 22 are particularly memory mapped or I/O-mapped, such that they can be interrogated by an external clinical programmer who is capable of reading out the contents of memory of the leadless pacemaker 1. The respective RAM blocks associated to the RAM event counters 51, 52 used to count the overflow counts for each hardware event counter 21, 22 are also readable by the external programmer.

The programmer uses the overflow counts of the RAM event counters 51, 52 as the higher order part of the total counts and the counts of the hardware event counters 21, 22 as the lower order part of the total counts, wherein particularly the total number of counts is equal to the product of the overflow counts and the known maximum number of counts of the associated hardware event counter 21, 22 plus the current count of the associated hardware event counter 21, 22.

The embedded system 3 is suitable for an arbitrary number n of input signals based on an arbitrary number of events En. Corresponding to the signal processing structure for signals based on the events E1 and E2, any further signal may processed by logic unit In, followed by hardware event counter 2*n*, storage of overflow bits in the first memory unit 30, transferring the overflow bits to the second memory unit 40 via data bus 60 for further processing by the CPU 2.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this disclosure, which is to be given the full breadth thereof. Additionally, the disclosure of a range of values is a disclosure of every numerical value within that range, including the end points.

LIST OF REFERENCE NUMERALS

1 Leadless pacemaker
2 Central processing unit
3 Embedded system
4 Electronic module
5 Energy storage
6 Electrical connection
7 Electrode
8 Fixation elements
9 Implant/explant port
11 First logic circuit
12 Second logic circuit
21 First hardware event counter
22 Second hardware event counter
30 First memory unit
40 Second memory unit
50 Random access memory (RAM)
51 First RAM event counter
52 Second RAM event counter
60 Data bus
70 Clock
C Clock data
E1 First event
E2 Second event
O Overflow
S Set operation
T Transfer operation

What is claimed is:

1. A leadless pacemaker comprising:
a central processing unit configured to control an operation of the leadless pacemaker,
a first logic circuit configured to generate event data based on a first event occurring during operation of the leadless pacemaker,
a first hardware event counter configured to be incremented if specific event data are generated by said first logic circuit,
a first memory unit comprising a first bit configured to be set if said first hardware event counter is incremented to a first maximum number of counts,
a second memory unit communicating with said first memory unit, wherein said central processing unit is configured to transfer said first bit to said second memory unit, and
a first RAM event counter in a random access memory of said leadless pacemaker, wherein said central processing unit is configured to increment said first RAM event counter if said first bit is transferred to the second memory unit.

2. The leadless pacemaker according to claim 1, wherein the leadless pacemaker further comprises a second logic circuit configured to generate event data based on a second event occurring during operation of the leadless pacemaker and a second hardware event counter configured to be incremented if specific event data are generated by said second logic circuit, wherein said first memory unit comprises a second bit configured to be set if said second hardware event counter is incremented to a second maximum number of counts, and wherein said central processing unit is configured to transfer said second bit to said second memory unit, and wherein said leadless pacemaker comprises a second RAM event counter in said random access memory of said leadless pacemaker, wherein said central processing unit is configured to increment said second RAM event counter if said second bit is transferred from the first memory unit to the second memory unit.

3. The leadless pacemaker according to claim 1, wherein said first event is describable by a binary variable, wherein said event data generated from said first event is a value of said binary variable.

4. The leadless pacemaker according to claim 1, wherein said first event is describable by a first binary variable and a second binary variable, wherein said event data generated from said first event is a third binary variable representing a specific combination of values of said first binary variable and said second binary variable.

5. The leadless pacemaker according to claim 1, wherein said first event is describable by a binary variable and a metric variable, wherein said event data generated from said first event represents a combination of a value of said binary variable and a range of said metric variable.

6. The leadless pacemaker according to claim 1, wherein said leadless pacemaker comprises a clock configured to generate clock data.

7. The leadless pacemaker according to claim 6, wherein said first memory unit is double buffered, such that its contents are transferrable to said second memory unit while clearing said first memory unit in a single operation, wherein said operation is clocked based on said clock data.

8. The leadless pacemaker according to claim 2, wherein said central processing unit is configured to transfer said first bit and/or said second bit to said second memory unit.

9. The leadless pacemaker according to claim 1, wherein said first hardware event counter and/or said second hardware event counter is memory mapped or I/O-mapped.

10. The leadless pacemaker according to claim 1, wherein said first memory unit and/or said second memory unit is a register or a latch, wherein particularly said second memory unit is a tristate latch.

11. A method for storing event data in a leadless pacemaker, particularly a leadless pacemaker according to claim 1, wherein event data are generated based on a first event occurring during operation of the leadless pacemaker, and wherein a first hardware counter is incremented if specific event data are generated based on said first event, and wherein a first bit in a first memory unit is set if said first hardware event counter is incremented to a first maximum number of counts, an wherein said first bit is transferred from the first memory unit to a second memory unit, and wherein a first RAM event counter in a random access memory of said leadless pacemaker is incremented if said first bit is transferred to the second memory unit.

12. The method according to claim 11, wherein further event data are generated based on a second event occurring during operation of the leadless pacemaker, and wherein a second hardware counter is incremented if specific event data are generated based on the second event, and wherein a second bit in said first memory unit is set if said second hardware event counter is incremented to a second maximum number of counts, and wherein said second bit is transferred from the first memory unit to a second memory unit, and wherein a second RAM event counter in said random access memory of said leadless pacemaker is incremented if said second bit is transferred to the second memory unit.

13. The method according to claim 11, wherein said first event is describable by a binary variable, and wherein said event data generated from said first event is a value of said binary variable, wherein particularly said first event is a pace delivered by the leadless pacemaker or a ventricular sense detected by the leadless pacemaker.

14. The method according to claim 11, wherein said first event is describable by a first binary variable and a second binary variable, wherein said event data generated from said first event is a third binary variable representing a specific combination of values of said first binary variable and said second binary variable, particularly wherein said first event is a cardiac cycle with an atrial sense and a ventricular pace.

15. The method according to claim 11, wherein said first event is describable by a binary variable and a metric variable, wherein said event data generated from said first event represents a combination of a value of said binary variable and a range of said metric variable, particularly wherein said first event is a cardiac cycle with an atrial sense and a time interval between atrial senses within a specific range.

* * * * *